United States Patent [19]

Bertin et al.

[11] Patent Number: 5,019,108
[45] Date of Patent: May 28, 1991

[54] MODULAR IMPLANT

[76] Inventors: Kim C. Bertin, 324 Tenth Ave., Suite 111, Salt Lake City, Utah 84103; Harry E. Rubash, 3601 Fifth Ave., Pittsburgh, Pa. 15213

[21] Appl. No.: 474,161

[22] Filed: Feb. 2, 1990

[51] Int. Cl.$^5$ ............................................. A61F 2/32
[52] U.S. Cl. ..................................................... 623/23
[58] Field of Search ....................... 623/16, 18, 19, 22, 623/23

[56] References Cited

U.S. PATENT DOCUMENTS

| D. 235,485 | 6/1975 | Amstutz . |
|---|---|---|
| 3,228,393 | 1/1966 | Michele . |
| 3,510,883 | 10/1967 | Cathcart, III . |
| 3,685,058 | 8/1972 | Tronzo . |
| 3,744,061 | 7/1978 | Frost . |
| 3,814,089 | 6/1974 | Deyerle . |
| 3,843,975 | 10/1974 | Tronzo . |
| 4,404,693 | 9/1988 | Zweymuller . |
| 4,636,214 | 1/1987 | Homsy . |
| 4,718,915 | 1/1988 | Epinette . |
| 4,778,475 | 10/1988 | Ranawat et al. . |
| 4,842,606 | 6/1989 | Kranz . |
| 4,865,608 | 9/1989 | Brooker, Jr. . |

FOREIGN PATENT DOCUMENTS 0041591 2/1981 European Pat. Off. .............. 623/23

OTHER PUBLICATIONS

Howmedica Publication "Howmedica Hip Fracture Stem System" of Griffne/Carr, Inc., Salt Lake City, Utah.
Zimmer Catalog "Prosthetic Implants" of Zimmer, Inc., Warsaw, Ind.
Product Brochure "Anatomic Hip Prosthesis" of Zimmer, Inc., Warsaw, Ind.

Primary Examiner—David J. Isabella
Attorney, Agent, or Firm—M. Reid Russell

[57] ABSTRACT

A modular hip implant for left or right side installation as a femoral implant portion of a hip prosthesis. The implant is preferably utilized in a surgical procedure addressing fractures of the femoral neck and may inclue a lateral opening formed through a proximal portion of the implant for receiving a fenestration plug for installation thereover. Which fenestration plug is for use where the implant is to be cemented in place, and is not installed when the implant is for friction seating implantation. For ease of installation, the implant includes a stem that tapers inwardly along three sides, the anterior, medial and posterior, to the implant end, the corners or junctions of which sides are rounded. The implant is also tapered at the proximal portion, inwardly from its lateral straight side to its medial side, for providing, when press fitted into a prepared medullary channel, a wedging therein. The proximal portion of which implant may be roughened to encourage cancellous tissue growth thereto, and includes a lateral hole therethrough that is to receive a tool for turning and lifting the implant for its removal. Adjacent to which hole is arranged a collar that is tapered inwardly from a wide circular circumference to above the opposite surfaces of the implant proximal portion, which taper allows for passage of a tool along the implant that is used for cutting through bone growth or cement to facilitate implant removal. A tapered neck extends at approximately a right angle from the surface of which collar that is for mounting a head thereon. Which neck is offset medially to where a selected head mounted on the neck will match the normal anatomy of a particular patient.

20 Claims, 3 Drawing Sheets

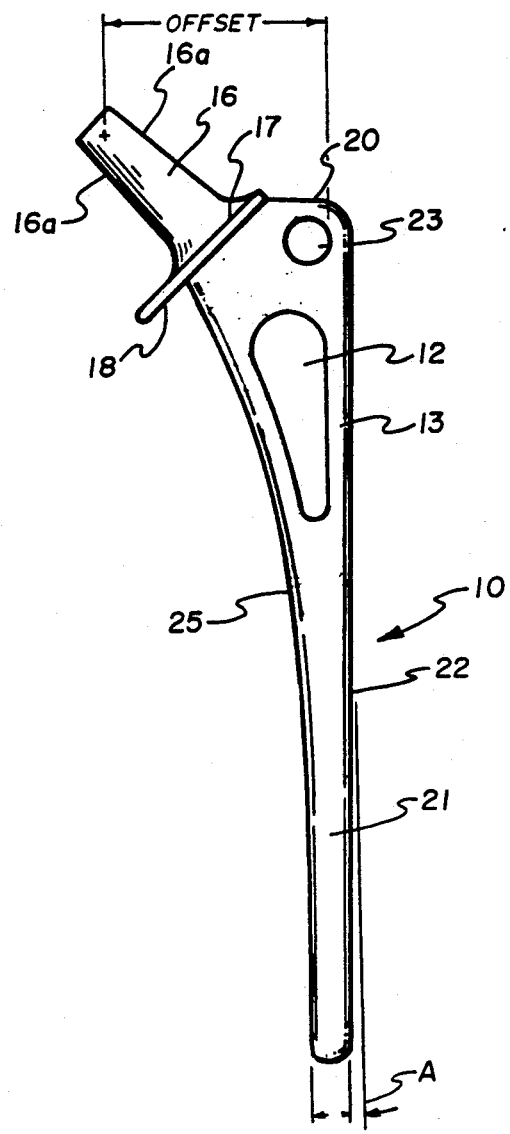
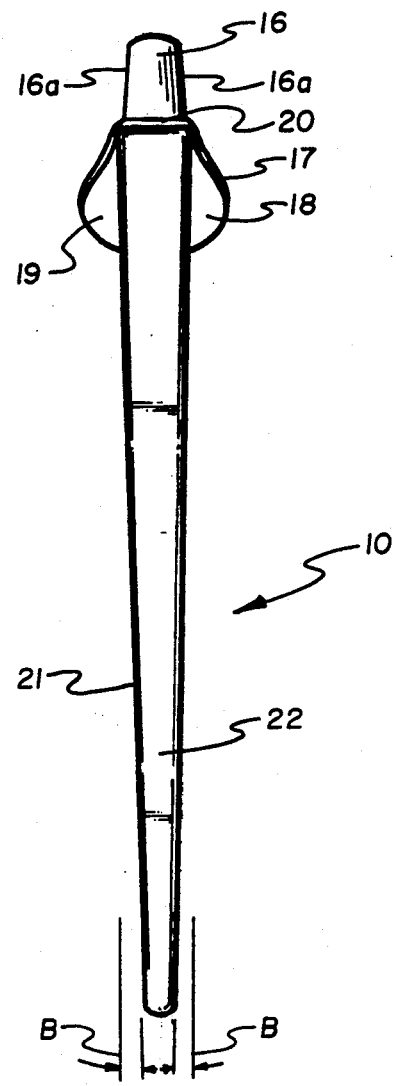
Fig. 3          Fig. 4
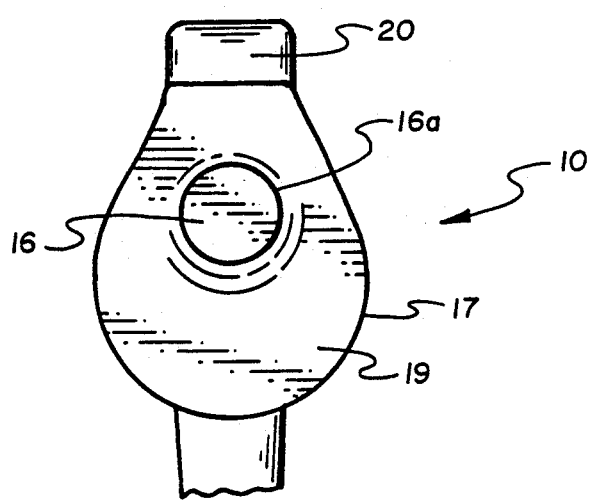
Fig. 5

MODULAR IMPLANT

BACKGROUND OF THE INVENTION

1. Field of the Invention

The present invention relates to femoral components for implantation in a hip arthroplasty.

2. Prior Art

Despite some early successes in utilizing bone ingrowth implants in hip arthroplasty, an implant commonly known as an AUSTIN-MOORE™ ™ femoral stem, and more recently a BIO-MOORE™ ™ modular endoprosthesis system, have continued to be used for the treatment of elderly patients who suffer femoral neck fractures. Certain problems and short term complications, however, are inherent with the use of both the AUSTIN-MOORE™ ™ and BIO-MOORE™ ™ femoral stems. For example, the implant is only available as an endo prosthesis and as such it is not modular for options as a total hip or biarticular. Also, there is often progressive acetabular cartilage resorption and protrusion of the endoprosthesis into the pelvis. Further, neck length adjustability is lacking in this device, thereby often necessitating a change in the patient's leg length with an alteration of abductor function. Finally, these earlier appliances come in both fenestrated and solid design, requiring the maintenance of a greater inventory than is required utilizing the implant of the present invention that is selectively configured as fenestrated or solid.

Additional to its being alternatively configured to be fenestrated or solid, it can also be press fitted or cemented in place. Further, it is not anteverted and thus the same unit can be utilized as either a right or left implant; it has a tapered neck that affords the surgeon, by an appropriate head selection, with the ability to adjust for both leg lengths and abductor tension; and it can be used as a bipolar, as an endoprosthesis, and, as necessary, with an acetabular component as a total hip. While the present invention utilizes new instrumentation, their use by a surgeon requires only slight alterations from their current surgical techniques.

BRIEF SUMMARY OF THE INVENTION

It is therefore a principal object of the present invention in a modular hip implant to provide a prosthesis that is desirable for treating femoral neck fractures, particularly in elderly patients.

Another object of the present invention is to provide a hip implant that can be selectively configured for utilization as a press fit or cement connected prosthesis and is sloped to wedge tightly in place when press fitted.

Another object of the present invention is to provide an implant that is not anteverted and accordingly can be utilized as either a right or left implant.

Another object of the present invention is to provide an implant that is configured to facilitate its removal by providing access to the channel it is installed in.

Still another object of the present invention is to provide an implant having a medially off-set neck to match the anatomy of most persons.

Still another object of the present invention is to provide an implant having an adjustment capability after installation so as to allow for the adjustment of both leg length and/or abductor tension.

Still another object of the present invention is to provide an implant where, with a selection of ends, the implant can be utilized as an endo, bipolar or total hip prosthesis.

Still another object of the present invention is to provide an implant that utilizes new and simple instrumentation and procedures for its implantation that are functionally like current techniques.

In accordance with the above objects the present invention is a modular hip implant that includes a stem for seating in a prepared intramedullary channel or canal. Which stem is somewhat rounded and is slightly tapered outwardly from the stem end along the anterior, medial and posterior stem sides and tapers inwardly linearly from a lateral straight side to the stem medial side to provide as a seated prosthesis a wedging into the medullary channel as a force is applied to drive the prosthesis into that channel when it is press fitted in place. The portions of the implant may be textured, as by bead blasting, or the like, for promoting bone growth thereto and includes a central opening. A continuous pier, ledge, or lip, or sections thereof, are included around that central opening wall for receiving a groove of a fenestration plug. Which groove is formed around the outer edge thereof. Which fenestration plug is for fitting in and covering over that central opening. With the fenestration plug in covering arrangement, the implant is suitable for being cemented in place. The fenestration plug is for preventing a flow-through of cement that would otherwise cross the implant mid-line, making removal difficult. Whereas, for a friction fit, it is desirable to leave the central opening open and accordingly the fenestration plug will not be used.

Where other implants have been anteverted thereby requiring the stocking of both left and right prosthesis, the implant of the present invention is not anteverted and can be used for either right or left implantation. Further, for providing a versatile appliance, the implant utilizes the Morris-tapered neck that accepts three different neck length modular femoral heads, affording a surgeon an ability to adjust the implant length.

Further, the neck is off-set a greater distance medially allowing for off-setting a head that is installed thereon as much as nine (9) mm beyond the off-set of earlier prosthesis. This capability allows the surgeon to match the normal anatomy of as many as ninety (90) percent of the population.

For facilitating implant removal, should such be necessary, the collar of the implant of the present invention is curved inwardly from a wide cantilevered portion for providing room for insertion of a tool along the implant sides to engage the cement and/or bone growth. Also for facilitating implant removal, the implant of the present invention provides an extraction hole formed through an implant center portion that is adjacent to a driving platform and implant neck.

DESCRIPTION OF THE DRAWINGS

In the drawings that illustrate that which is presently regarded as the best mode for carrying out the invention:

FIG. 3 is a right side elevation view of the modular hip implant of FIG. 1;

FIG. 4 is a rear end elevation view of the modular hip implant of FIG. 1;

FIG. 5 is a top plan view of the modular hip implant of FIG. 1, the lower portion of the stem thereof shown as broken away;

FIG. 8 (B) is a side elevation view of a femoral head caliper; and

DETAILED DESCRIPTION

Figure 1:
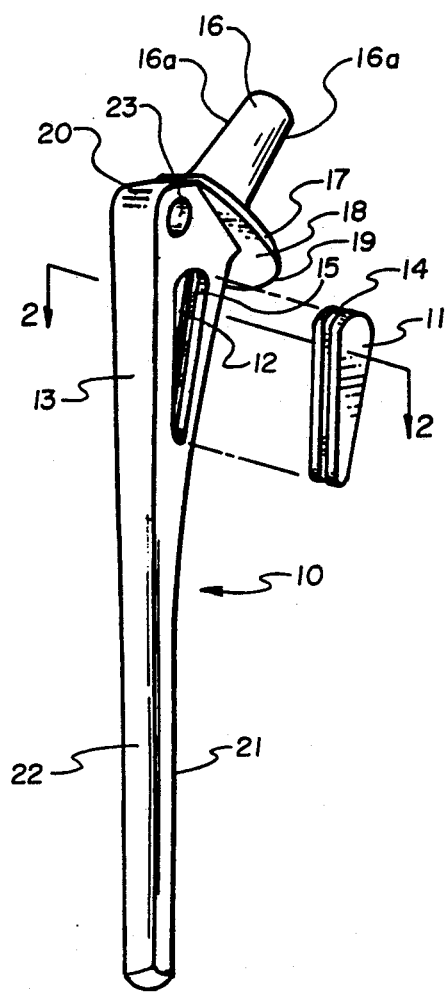
FIG. 1 is a profile perspective view of the modular hip implant of the present invention.
Figure 2:
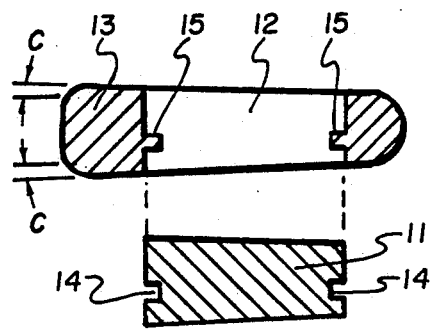
FIG. 2 is a cross-sectional view taken along the line 2—2 of FIG. 1.

FIG. 1 shows a preferred embodiment of a modular hip implant 10 of the present invention, hereinafter referred to as implant. Implant 10 has a capability for being utilized as either a cemented or uncemented left or right side prosthesis. For use as cemented prosthesis, a fenestration plug 11 is provided for fitting into and filling a fenestration or central opening 12 that is formed through the implant central or proximal portion 13. For use in an uncemented or friction fit arrangement the fenestration plug 11 is removed, and the central opening 12 left open. The central opening promotes, an increased interdigitation with cancellous bone of the proximal femur. So arranged, with time, cancellous tissue will grow through the fenestration, or central opening 12, further securing the implant in place.

Where the implant 10 is to be cemented in place, it is undesirable that such cement should cross the implant midline. Accordingly, prior to installation, the fenestration plug 11 is installed to fill the central opening 12. In such installation, as shown best in FIG. 2, the fenestration plug 11 is arranged to allow a circumferential groove or groove sections 14 to receive a ridge 15 that is formed as a continuous ridge or in sections within and around the wall of the central opening 12. Or, the groove or groove sections can be included in the wall of the central opening with the ridge or ridge section formed around the fenestration plug, or other coupling arrangement can be used within the scope of this disclosure Preferably, to facilitate flexure and to minimize weight, the fenestration plug 11 is formed of a plastic material, such as a polyethylene, and may be biodegradable within the scope of this disclosure. Further the fenestration plug may be metal covered with a porous coating for prompting cancellous bone growth thereto within the scope of this disclosure.

As set out above, implant 10 is preferably for left or right side installation and accordingly it is not anteverted. Further, for enhancing its utility, a neck 16, that is set at a standard one hundred thirty five (135) degrees from the horizontal, is tapered as with a Morris-taper, as shown at 16a, inwardly from the neck base to its top end. This taper is for receiving and seating different diameters of head implants or endoprosthetic heads, not shown, to afford, by that head selection, a surgeon with the ability to adjust both leg lengths and abductor tension.

Further to the present invention, the neck of implant 10 is set further medially than other implants to give a surgeon greater capability to match the normal patient anatomy. As set out in the comparison charts below, the implant 10, with appropriate head selection, affords the surgeon the ability to select an offset of the head center to the stem longitudinal center line, as illustrated in FIG. 3 of from 33 mm to 52 mm. The off-set range of thirty three (33) mm to fifty two (52) mm that is for provided by implant 10 allows the surgeon to match the anatomy of a large group (ninety percent or more) of the population. This off-set range as set out in the charts below, is none (9) mm greater than can be achieved by any of the Moore stems. Herein below are set out comparison charts comparing different stem lengths of Moore stems with different lengths of the implant 10 of the present invention.

| | OFF-SET/NECK LENGTH CHART | | | |
|---|---|---|---|---|
| Anatomic Stem | Head Size (mm) Moore Stem | Stem Length (mm) | Off-Set (mm) S M L | Neck Length (mm) S M L |
| 4005 | 38 | 127 | 36 | 19 |
| 4005 | 40 | 127 | 39 | 23 |
| 4005 | 41 | 127 | 39 | 24 |
| 4005 | 42 | 127 | 39 | 24 |
| 4005 | 43 | 127 | 40 | 25 |
| 4005 | 44 | 127 | 40 | 25 |
| 4005 | 45 | 140 | 39 | 26 |
| 4005 | 46 | 140 | 40 | 27 |
| 4005 | 47 | 140 | 40 | 27 |
| 4005 | 48 | 140 | 41 | 27 |
| 4005 | 49 | 140 | 41 | 28 |
| 4005 | 50 | 152 | 40 | 28 |
| 4005 | 51 | 152 | 41 | 29 |
| 4005 | 52 | 152 | 41 | 29 |
| 4005 | 53 | 152 | 42 | 30 |
| 4005 | 54 | 152 | 42 | 30 |
| 4005 | 55 | 152 | 42 | 31 |
| 4005 | 57 | 152 | 43 | 32 |
| 4005 | 60 | 152 | 44 | 33 |
| | 63 | 152 | 43 | 33 |

| Implant 10 | Stem Length (mm) | Offset (mm) S* M* L* | | | ENDO.* | Neck Length S* M* L* | | | ENDO.* |
|---|---|---|---|---|---|---|---|---|---|
| 4555-10 | 135 | 33 | 38 | 43 | 39 | 22 | 30 | 37 | 31 |
| 4555-20 | 145 | 36 | 41 | 46 | 42 | 26 | 33 | 40 | 34 |
| 4555-30 | 155 | 39 | 44 | 49 | 45 | 28 | 36 | 42 | 36 |

| | | | | | | | | | |
|---|---|---|---|---|---|---|---|---|---|
| 4555-40 | 165 | 42 | 47 | 52 | 48 | 31 | 38 | 45 | 39 |

*Note - The different offsets and neck lengths are provided by the head selection.

The charts, additional to showing the offset capabilities of implant 10 as compared to the Moore stem further show the versatility of the present invention. Four (4) stems of the present invention provide the surgeon with a full range of size selection that compares to twenty (20) of the Moore stems.

Like many earlier implants, the implant 10 includes a collar 17 that is at essentially a right angle to the neck 16 longitudinal axis. Which neck preferably projects outwardly at approximately a right angle centrally from the collar top or upper surface. An undersurface 18 of which collar 17 is flat for fitting over the prepared proximal femur end when the implant is installed therein. As shown best in FIGS. 1, 4 and 5, unique to implant 10, collar 17 has a wide circular circumference 19, and tapers inversely therefrom inwardly along opposite sides to intersect a shoulder 20. A low profile collar 17 is thereby provided that decreases a chance of impingement and permits insertion of an ancillary bone graft. Which inwardly sloping collar sides further provide ease of access to tools, such as a chisel, or power instrument, manipulated by a surgeon to fit along the implant for cutting through cancellous bone growth and/or cement so as to break the implant loose for its removal.

With the implant stem 21 fitted into the femur intramedullary channel or canal, the shoulder 20, adjacent to the collar 17 and neck 16, provides a flat surface whereagainst a tool, such as a hammer, can be used to apply a force for driving the implant stem along that intramedullary channel or canal.

Shown best in FIGS. 1 and 3, the implant 10 includes a lateral straight flat side 22 that is formed at approximately a right angle from the flat surface of shoulder 20 and extends the length of the implant. Which flat side becomes one side of the stem 21, below the proximal portion 13. A round hole 23 is formed through the proximal portion 13, that is spaced on the bias from the junction of shoulder 20 and flat side 22. Hole 23 is for receiving a tool, not shown, that is fitted therethrough and is for use by a surgeon for applying a torquing and/or lifting force to the implant during its removal.

Shown best in FIGS. 3 and 4, the implant stem 21 incorporates approximately a five (5) degree inward taper, from the stem top at shoulder 20 to the stem end 24, on the three sides thereof, the anterior, medial and posterior sides shown as angles A and B. Which taper not only facilitates implant insertion and provides a tight wedge fit proximally to prevent the prosthesis from subsiding or tilting and achieves proximal canal fill so as to achieve prosthesis stability. The distal stem at side 25 is shown to taper in the anterior aspect to compensate for the normal anterior bow of the femur, thereby preventing contact with the femoral cortex at the time of its insertion. Also, as shown best in FIG. 2, the implant, at its mid-portion, tapers inwardly from the lateral straight side 22 to the medial side 25 at an angle of approximately five (5) degrees, shown as angle C. This taper provides a wedging action at the wider portion of the implant for further locking it into the narrower portion of the prepared medullary channel as a weight or force is applied.

Figure 9:
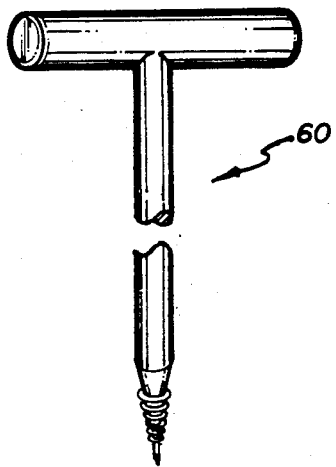
FIG. 9 is a profile perspective view of a femoral head extractor.
Figure 8B:
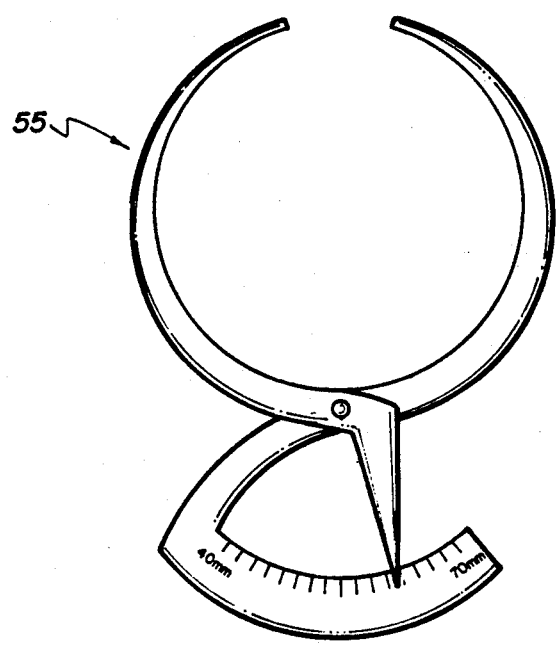
FIG. 8 (A) is a top plan view of a go, no-go femoral head gauge.
Figure 8A:
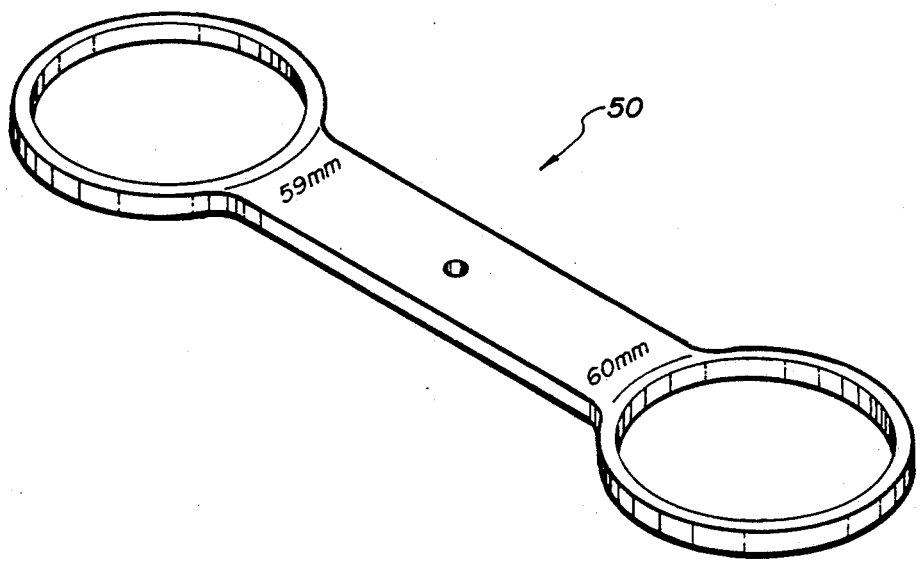

The implant 10 is preferred for use as an endoprosthesis or biarticular for treatment of a femoral neck fracture. The surgical procedure for preparing the proximal femur and implant size selection are simple, essentially standard, and depend upon surgeon preference. Preliminarily, in such surgical procedure, the hip capsule is opened and the femoral head that has broken across its neck is distracted from the acetabulum. This distraction is preferably accomplished utilizing a femoral head extractor 60, like that shown in FIG. 9, that is of the corkscrew variety, and is turned into the broken neck until it is seated. Thereafter a tensile force can be applied through the extractor 60 to pull the femoral head from the acetabulum. The femoral head is then sized by utilizing a go, no-go gauge 50, like that shown in FIG. 8(A), or a caliper 55, like that shown in FIG. 8(B), for determining proper sizing of the head or articular replacement, not shown.

Figure 6:
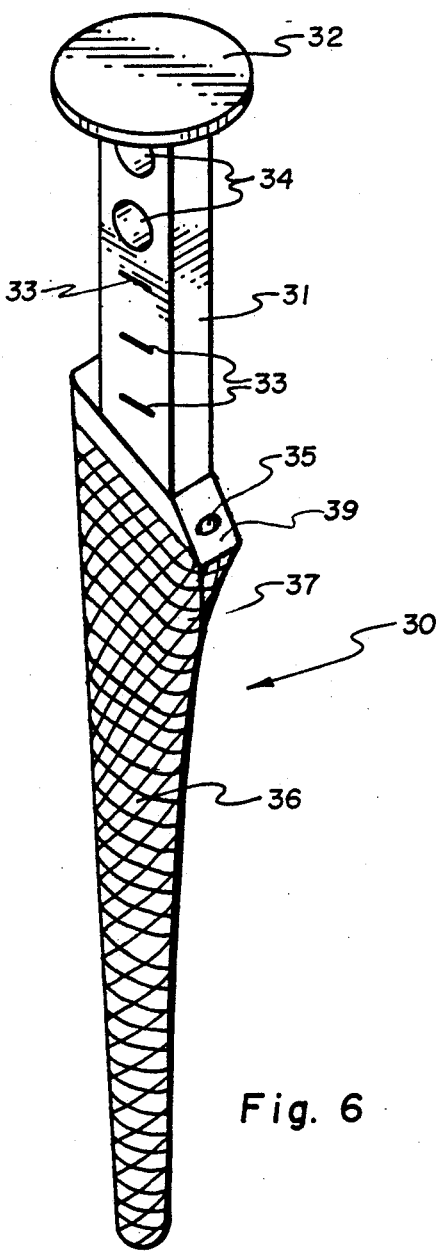
FIG. 6 is a profile perspective view of a rasp that is suitable for preparing a femur intramedullary channel to receive the modular hip implant and for use in determining a proper modular hip implant size selection.

With the proximal femur exposed it is opened utilizing a box osteotome, not shown, or a like instrument, that provides for a simple and quick removal of the femur lateral neck at the trochanter. Following this removal, that opens the femur intramedullary channel or canal, a series of rasps, like a rasp 30 shown in FIG. 6, are sequentially inserted from lesser to greater size or diameter. In practice, a pre-operative planning template can be used to afford a surgeon with a rough guide for estimating a proper size or sizes selection of rasp 30, and the proper size of implant 10, as well as to estimate the level of the femoral osteotomy cut.

Figure 7:
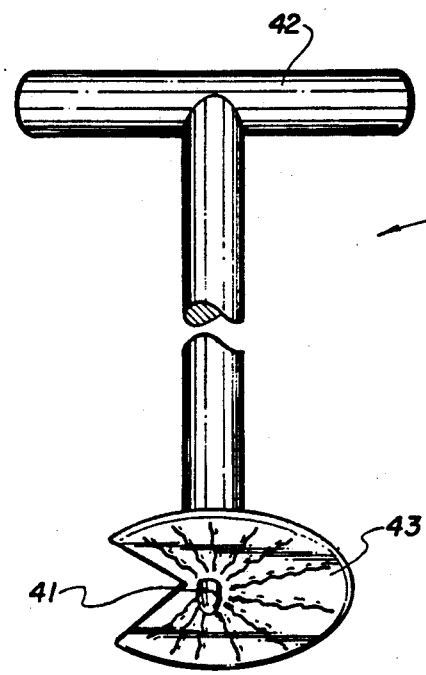
FIG. 7 is a profile perspective view of a calcar reamer.

Shown in FIG. 6, the rasp 30 is essentially a standard rasp that is approximately one (1) mm less in cross section than the selected implant stem to be fitted in the medullary channel or canal, which rasp 30 has a solid rectangular handle 31 and flat head end 32. The rasps handle 31 preferably includes parallel proximal engraved lines or marks 33 that are to indicate the level of the center of the femoral head. Which marks 33 are to be compared to the tip of the greater trochanter. With the rasp 30 properly installed in the intramedullary channel or canal, the medial base of the rasp 30 can serve as a guide for a final femoral osteotomy. A saw, such as a HALL ™ oscillating saw, can then be used to cut the femoral neck. If the file or crosshatched portion 36 of rasp 30 is acceptably seated, a hole 35 on the medial side of rasp handle 31 will be acceptably positioned for receiving an axial pin of a hand held calcar reamer 40, as shown in FIG. 7. A pin 41 of the reamer is to fit in a hole 35 of rasp 30, functioning as a pivot. A surgeon, turning handle 42 turns a serated blade around on the under surface of a disk 43 back and forth, planing the femoral neck. Which reamer 40 is for performing a medial finishing cut on the femoral neck. This preparation step finalizes the press fit machining and guarantees a flat contact of the stem collar 17 to the prepared surface. Should movement of the rasp 30 be required, or to facilitate its removal, extraction holes 34 are provided for receiving a tool such as a rod or bar, not shown, for manual turning or lifting by a surgeon.

Alternatively, should it be determined that the neck osteotomy needs to be adjusted, the surgeon can elect to place a saw blade parallel to a fitted rasp angled portion 39 for guiding the cut on the femoral neck. Thereafter, the calcar reamer 40 can be utilized to finish the medial cut. The implant 10 is to serve as its own provisional for testing fit.

For a cemented implant 10, an implant of the same size as the intramedullary channel or canal can be selected. Or, if it is a large voluminous intramedullary channel or canal, or should the surgeon desire a large cement mantle, then a lesser size implant 10 can be selected. For a cemented implant 10 the fenestration plug 11 is preferably left in or snapped in place prior to cementing. For a friction fit implantation, the fenestration plug 11 is preferably removed, and a size of implant 10 will be carefully selected to exactly fit in the intramedullary channel or canal. The implant 10 fit should be such as to withstand a torsional force application without micromovement. The implant tapered neck 16a, for example a Morris-taper, allows for a selection of a particular endoprosthetic head to fit thereon for providing a surgeon with a final length adjustment capability.

As discussed hereinabove and shown in the offset/neck length charts, set out earlier herein, the implant 10 will preferably be available in approximately four (4) sizes, and with proper head selection, provides a surgeon with a full range of length adjustment and head offset capability.

While a preferred embodiment of the invention in a modular hip implant and its use has been shown and described herein, it should be apparent that the present disclosure is made by way of example only and that variations to the invention are possible within the scope of this disclosure without departing from the subject matter coming within the scope of the following claims and a reasonable equivalency thereof, which claims we regard as our invention.

We claim:

1. A modular hip implant comprising, a femoral implant that includes a stem for fitting in a prepared femoral canal, which said stem extends from a proximal portion, wherethrough is formed a lateral opening; a fenestration plug is arranged for fitting across said lateral opening and includes means for releasably locking said fenestration plug in said lateral opening consisting of a ridge means that is formed within said lateral opening and is for fitting in a groove means that is formed around the edge of said fenestration plug; and a neck means that extends outwardly from said proximal portion for receiving a head thereon.

2. A modular hip implant as recited in claim 1, wherein three of the stem sides, the anterior, medial and posterior sides, taper inwardly from the proximal portion to a stem end at approximately five (5) degrees from the vertical, and the corners or junctions of which sides are rounded.

3. A modular hip implant as recited in claim 1, wherein the stem proximal portion tapers inwardly linearly from its lateral straight side to its medial side at an angle of approximately five (5) degrees.

4. A modular hip implant as recited in claim 1, further including a tapered neck as the neck means that is offset medially from the stem longitudinal center axis to where a selected head mounted on the neck will match the normal anatomy of a patient.

5. A modular hip implant as recited in claim 4, further including, with the proximal portion surface, a flat shoulder that is formed at approximately ninety (90) degrees to the stem longitudinal axis; and a collar that is arranged across an end of said proximal portion and adjacent to said flat shoulder and wherefrom the tapered neck extends.

6. A modular hip implant as recited in claim 5, further including a hole formed through the proximal portion, adjacent to the flat shoulder, for receiving a tool means fitted therethrough that is for manual turning and lifting of the implant.

7. A modular hip implant as recited in claim 6, wherein the collar has a circular circumferential end that is spaced apart from the tapered neck, and said collar tapers inversely inwardly, which taper terminates at opposite sides of the shoulder.

8. A modular hip implant as recited in claim 1, wherein the fenestration plug is formed of a flexible material.

9. A modular hip implant as recited in claim 8, wherein the fenestration plug is formed of a plastic material.

10. A modular hip implant as recited in claim 1, wherein the fenestration plug is formed of a metal whereto a porous coating is applied.

11. A modular hip implant comprising a femoral implant that includes a stem for fitting in a prepared femoral canal, that extends from a proximal portion, and includes a lateral opening formed through the proximal portion; a fenestration plug arranged for fitting across said lateral opening and includes means for releasably locking said fenestration plug in said lateral opening consisting of a ridge means that is formed in sections within said lateral opening and is for fitting in a groove means that is formed around the edge of said fenestration plug and a neck means that extends outwardly from said proximal portion for receiving a head thereon.

12. A modular hip implant as recited in claim 11, wherein three of the stem sides, the anterior, medial and posterior sides, taper inwardly from the proximal portions to a stem end at approximately five (5) degrees from the vertical, and the corners or junctions of which sides are rounded.

13. A modular hip implant as recited in claim 12, wherein the stem proximal portion tapers inwardly linearly from its straight lateral side to its medial side at an angle of approximately five (5) degrees.

14. A modular hip implant as recited in claim 12, wherein the neck means is offset medially from the stem longitudinal center axis and is tapered to where the combination of a selected head for the implant will match the normal anatomy of a patient.

15. A modular hip implant as recited in claim 12, further including, with the proximal portion surface, a flat shoulder that is formed at approximately ninety (90) degrees to the stem longitudinal axis; and a collar that is arranged across an end of said proximal portion and adjacent to said flat shoulder and wherefrom the neck means extends.

16. A modular hip implant as recited in claim 15, further including a hole formed through the proximal portion, adjacent to the flat shoulder, for receiving a tool means fitted therethrough that is for manual turning and lifting of the implant.

17. A modular hip implant as recited in claim 16, wherein the collar has a circular circumferential end that is spaced apart from the tapered neck, and said collar tapers inversely inwardly, which taper terminates at opposite sides of the shoulder.

18. A modular hip implant as recited in claim 12, wherein the fenestration plug is formed of a flexible material.

19. A modular hip implant as recited in claim 18, wherein the fenestration plug is formed of a plastic material.

20. A modular hip implant as recited in claim 12, wherein the fenestration plug is formed of a metal whereto a porous coating is applied.

* * * * *